United States Patent [19]

Yoshikuni et al.

[11] Patent Number: 4,755,523
[45] Date of Patent: Jul. 5, 1988

[54] ABIETAMIDE DERIVATIVES

[75] Inventors: Yoshiaki Yoshikuni, Uji; Shoichi Chokai, Kameoka; Yukio Fujita, Takatsuki; Takayuki Ozaki, Moriyama, all of Japan

[73] Assignee: Nippon Shinyaku Co., Ltd., Japan

[21] Appl. No.: 15,287

[22] Filed: Feb. 17, 1987

[30] Foreign Application Priority Data

Feb. 15, 1986 [JP] Japan .................................. 61-031585
Feb. 15, 1986 [JP] Japan .................................. 61-031586

[51] Int. Cl.$^4$ .................. C07D 277/46; C07D 231/40; A61K 31/415; A61K 31/425
[52] U.S. Cl. ..................................... 514/371; 548/195; 548/375; 514/407
[58] Field of Search ................ 548/145, 375; 564/180, 564/188; 514/371, 407

[56] References Cited
FOREIGN PATENT DOCUMENTS
133799 1/1979 Fed. Rep. of Germany ...... 548/195

Primary Examiner—Robert Gerstl
Attorney, Agent, or Firm—Jacobs & Jacobs

[57] ABSTRACT

Abietamide derivatives of the formula I

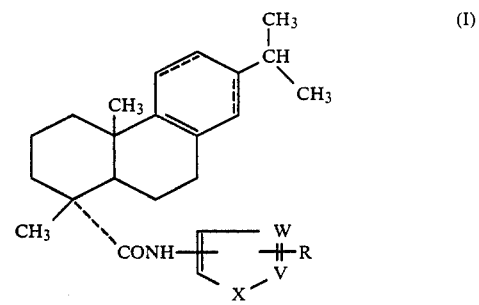

wherein X is NZ wherein Z is hydrogen, alkyl, unsubstituted or substituted phenyl or X is a sulphur atom; when X is NZ, V is nitrogen, W is π, and R is hydrogen or alkyl and when X is a sulphur atom, V is ⫪, W is nitrogen, and R is hydrogen, alkyl, phenyl or —CH$_2$COOR'; wherein R' is hydrogen or alkyl and ==== is a single or double bond, are useful for treating hyperlipemia and particularly for the prevention and therapy of arteriosclerosis.

51 Claims, No Drawings

ABIETAMIDE DERIVATIVES

The present invention is concerned with abietamide derivatives which have been found to be useful in the treatment of hyperlipemia in humans and animals. Japanese Laid Open Application Sho-51/026864 describes N-(2,6-dimethylphenyl) Δ⁸-dihydroabietamides which inhibit absorption of extrinsic cholesterol from the intestinal tract but do not inhibit the biosynthesis of cholesterol. It has now been discovered that abietamide derivatives of the formula I

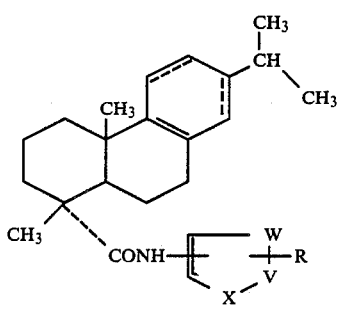

wherein X is NX wherein Z is hydrogen, alkyl, perfereably lower alkyl, or phenyl unsubstituted or substituted, wherein the preferred substituents are halo or lower alkyl or X is a sulphur atom and when X is NZ, V is nitrogen, W is ⫞ , and R is hydrogen or alkyl, preferably lower alkyl, and when X is a sulphur atom, V is ⫟ , W is nitrogen, and R is hydrogen, alkyl, prefereably lower alkyl, phenyl or —CH₂COOR'; wherein R' is hydrogen or lower alkyl and ═══ is a single or a double bond are useful for treating hyperlipemia in humans and animals and in particular have been found to inhibit the absorption of extrinsic cholesterol from the intestinal tract and to inhibit cholesterol biosynthesis and to accelerate anobolic excretion of cholesterol. Therefore, the compounds, pharmaceutical compositions, and methods of use, according to the present invention, are particularly useful for lowering cholesterol and are useful in the prevention and therapy of arteriosclerosis.

According to one embodiment of the present invention X is NZ wherein Z is hydrogen, straight or branch chain alkyl of 1-4 carbon atoms, or phenyl unsubstituted or substituted by halo or alkyl of 1-4 carbon atoms and R is hydrogen or straight or branched chain alkyl of 1-4 carbon atoms.

According to another embodiment of the present invention X is sulphur and R is hydrogen, straight or branch chain alkyl of 1-4 carbon atoms, phenyl or —CH₂COOR' wherein R' is hydrogen or straight or branch chain alkyl of 1-4 carbon atoms.

Preferred alkyl substituents for Z, R and R' include straight or branch chain alkyl of 1-4 carbon atoms such as methyl, ethyl, n-propyl, isopropyl, n-butyl, iso-butyl, sec-butyl and tert-butyl. When Z is phenyl, it may have any number of substitutents at any of the positions. Preferred substituents on the phenyl ring are halo, i.e. chloro, bromo, fluoro and iodo or alkyl, preferably straight or branch chain alkyl of 1-4 carbon atoms, including those groups specifically mentioned above.

The compounds of the present invention can be produced by the condensation of Δ⁸-dihydroabietic acid (II) or dehydroabietic acid (III) (hereinafter referred to as resin acids), with the corresponding amines.

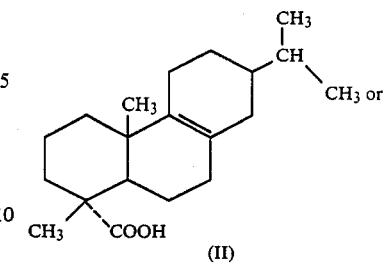

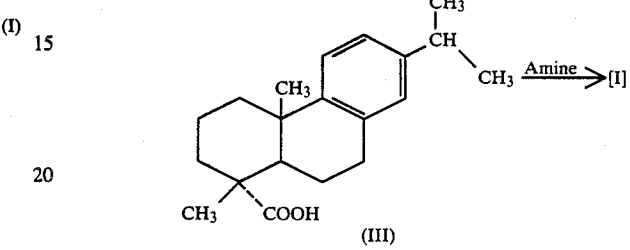

This amidation reaction may be carried out by procedures per se known such as, for example, by subjecting reactive derivatives such as an acid anhydride or acid halide of (II) or (III) to a suitable reaction. When an acid halide is used, the reaction may preferably be carried out in a solvent such as, for example, an aromatic hydrocarbon such as toluene and benzene; an ether such as dioxane; or a nonprotonic polar solvent such as acetonitrile and N,N-dimethylformamide. Preferably the temperature is from −10° C. to 100° C., preferably from −5° C. to 10° C. It is preferred that the reaction be carried out in the presence of a base such as an inorganic base such as potassium hydroxide or sodium hydroxide or in the presence of an organic base such as N,N-dimethylaniline or triethylamine.

The reaction time, according to the process of the present invention, may vary depening on the type of resin acid halide and amine used and upon the reaction temperature but generally the reation time would range from 1-72 hours. The amount of amine used is 1 to 1.5 moles to 1 mole of the resin acid halide. Equimolar sodium hydride or potassium hydride may be added thereto to accelerate the reaction and to increase the yield. The compounds the formula I according to the present invention, thus obtained may be isolated and purified by procedures per se known such as, for example, concentration, liquid property conversion, dissolution into different solvents, extraction with a solvent, crystallization, recrystallization, fractional distillation, chromatography, and the like. The starting material of the formula (II) used in the process of the present invention may be readily produced by a method per se known (see J. Org. Chem. 34, 1550, 1969), from a mixture mainly composed of Δ⁸⁽¹⁴⁾-dihydroabietic acid (VII). This mixture which contains Δ⁸⁽¹⁴⁾-dihydroabietic acid (VII) may be obtained by a catalyic reduction of palustric acid (IV), levopimaric acid (V), abietic acid (VI) or pine resin.

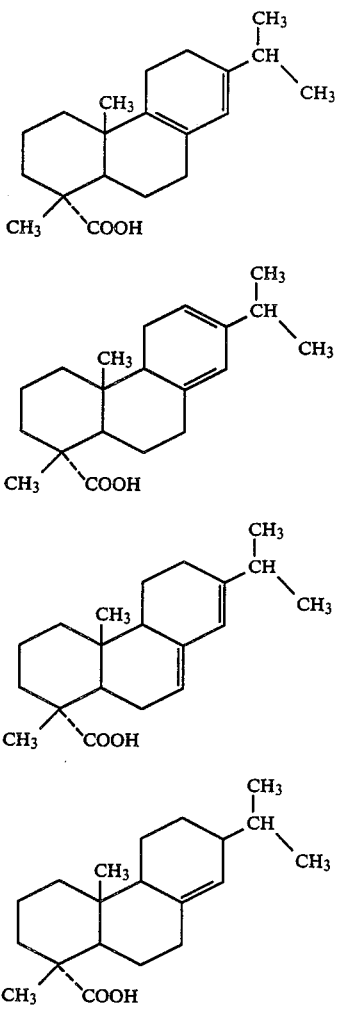

Starting material of the formula (III) may be obtained from commercially available disproportionated resin by procedures per se known (see J. Org. Chem. 31, 4246, 1967). Amines which are other reactants may be obtained commercially or may be produced by procedures per se known.

When the compounds of present invention are administered to humans and animals, it may be administered per se or more preferably as a pharmaceutical composition containing 0.1 to 99.5% (preferably 0.5 to 90%) of said compound in combination with a pharmaceutically acceptable carrier.

As to a carrier, one or more liquid, solid or semisolid diluents, fillers and other auxiliary agents for pharmaceutical preparations may be used. The pharmaceutical composition is preferably administered in a unit dose form. The present invention compound may be given per os, into tissue, from local part or via rectum. The composition is, of course, to be administered in a form suitable for each route of administration such as, for example, oral agent, injection and suppository. For example, oral administration is most preferred.

The dose as to a therapetuic agent for arteriosclerosis is to be preferably adjusted by taking the state of the patient (such as age and body weight), administration route, and type and degree of the disease into consideration. Generally it is within a range of 0.5 to 5.0 grams per day for the average human adult and more preferably from 1.0 to 2.0 grams. The dosage may, depending on a spasmatical history of the patient, the severity of the condition and the usual factors taken into consideration in administering therapeutic substances to humans and animals, be higher or lower than the above range. The dose may be divided and administered 2 or 3 times a day.

The following nonlimitative examples more particularly illustrate the present invention:

EXAMPLE 1

N-(1-phenylpyrazol-5-yl)-$\Delta^8$-dihydroabietamide $\Delta^8$-Dihydroabietic acid (298.4 g) was dissolved in 600 ml of benzene by warming. The solution was gently refluxed with stirring and 349.8 g of thionyl chloride was dropped thereinto during about 1 hour. The mixture was refluxed for 2 hours more after the dropping was completed. Benzene and an excess of thionyl chloride were removed by evaporation in vacuo. The residue was dissolved in 300 ml of dry dioxane and the solution was stirred and cooled with ice. A mixture of 156.0 g of 1-phenyl-5-aminopyrazole, 119.0 g of triethylamine and 200 ml of dioxane was dropped thereinto during about 1 hour. After the dropping was completed, the mixture was made to reacted by stirring at room temperature for 4 hours. White crystals separated out therefrom were collected by filtration. The mother liquor was concentrated to remove dioxane and the residue was crushed and washed with 100 ml of benzene. This was combined with the previously-obtained crystals and washed with 300 ml of methanol to give 388 g of white crystals, which were washed with water, dried and recrystallised from chloroform. The yield was 304 g (70%). Melting point 182°–183° C.

Elem. Anal.: $C_{29}H_{39}N_3O$ (Mol.Wt445.65); Calcd. (%): C 78.16 H 8.82 N 9.43; Found (%): C 78.08 H 8.99 N 9.46.

Using a procedure analogous to that described above, the following compounds were produced.

N-(1-Phenylpyrazol-5-yl)dehydroabietamide (m.p. 179°–182° C.)

Elem. Anal.: $C_{29}H_{35}N_3O$ (Mol.Wt441.62); Calcd. (%): C 78.87 H 7.99 N 9.52; Found (%): C 78.53 H 8.04 N 9.32.

N-(1-Methylpyrazol-5-yl)-$\Delta^8$-dihydroabietamide (m.p. 159° C.)

Elem. Anal.: $C_{24}H_{37}N_3O$ (Mol.Wt383.58); Calcd. (%): C 75.15 H 9.72 N 10.95; Found (%): C 75.46 H 9.89 N 10.56.

N-[1-(2-Chloro)phenylpyrazol-5-yl]-$\Delta^8$-dihydroabietamide (m.p. 159°–160° C.)

Elem. Anal.: $C_{29}H_{38}N_3OCl$ (Mol.Wt480.09); Calcd. (%): C 72.55 H 7.98 N 8.75; Found (%): C 72.51 H 8.07 N 8.75.

N-(1-p-Tolyl pyrazol-5-yl)-$\Delta^8$-dihydroabietamide (m.p. 171°–172° C.)

Elem. Anal.: $C_{30}H_{41}N_3O$ (Mol.Wt459.67); Calcd. (%): C 78.39 H 8.99 N 9.14; Found (%): C 78.13 H 9.19 N 9.12.

N-(1-p-Tolylpyrazol-5-yl)dehydroabietamide (m.p. 147°–149° C.)

Elem. Anal.: $C_{30}H_{39}N_3O$ (Mol.Wt457.66); Calcd. (%): C 78.33 H 8.59 N 9.18; Found (%): C 79.14 H 8.60 N 8.87.

N-(1-p-Tolyl-3-methylpyrazol-5-yl)dehydroabietamide (m.p. 122°–124° C.)

Elem. Anal.: $C_{31}H_{39}N_3O$ (Mol.Wt469.67); Calcd. (%): C 79.28 H 8.27 N 8.95; Found (%): C 78.66 H 8.52 N 8.80.

EXAMPLE 2

2-Dehydroabietoylamino-4-methylthiazole

Dehydroabietic acid chloride obtained from 29.54 g of dehydroabietic acid and 25 g of oxalic acid chloride was made to react with 15.06 g of 2-amino-4-methylthiazole at room temperature for 3 days in 100 ml of methylene chloride in the presence of 10.12 g of triethylamine. The reaction solution was washed with each 50 ml 5% hydrochloric acid twice, then washed with water, dried over anhydrous magnesium sulphate, and filtered. Methylene chloride was evaporated from the filtrate in vacuo to give pale brown oil. This was subjected to a silica gel column chromatography and eluted with benzene. Benzene was removed from the eluate in vacuo to give colourless oil, which was dried in vacuo to afford 13.5 g of colourless powder.

$IR\nu_{max}^{KBr}$ $(cm^{-1})$: 3340 (NH), 1620 (CO).

Elem. Anal.: $C_{24}H_{32}N_2O$ (Mol.Wt396.59); Calcd. (%): C 72.69 H 8.13 N 7.06; Found (%): C 72.32 H 7.98 N 7.15.

Using a procedure analagous to that described above, the following compounds were produced.

EXAMPLE 3

N-(Thiazol-2-yl)-$\Delta^8$-dihydroabietamide

Oil $IR\nu_{max}^{film}$ $(cm^{-1})$ 1620.

Elem. Anal.: $C_{23}H_{34}N_2OS$ (Mol.Wt386.59); Calcd. (%): C 71.46 H 8.86 N 7.25; Found (%): C 71.71 H 9.03 N 7.31.

EXAMPLE 4

N-(4-Methylthiazol-2-yl)-$\Delta^8$-dihydroabietamide

Oil $IR\nu_{max}^{film}$ $(cm^{-1})$ 1620.

Elem. Anal.: $C_{24}H_{36}N_2OS$ (Mol.Wt400.60); Calcd. (%): C 71.95 H 9.06 N 6.99; Found (%): C 72.03 H 9.15 N 7.11.

EXAMPLE 5

N-(Thiazol-2-yl)dehydroabietamide

Oil $IR\nu_{max}^{film}$ $(cm^{-1})$ 1620.

Elem. Anal.: $C_{23}H_{30}N_2OS$ (Mol.Wt382.56); Calcd. (%): C 72.21 H 7.90 N 7.32; Found (%): C 72.51 H 8.05 N 7.52.

EXAMPLE 6

N-(4-Phenylthiazol-2-yl)dehydroabietamide

Oil $IR\nu_{max}^{film}$ $(cm^{-1})$ 1623.

Elem. Anal.: $C_{29}H_{34}N_2OS$ (Mol.Wt458.66); Calcd. (%): C 75.94 H 7.47 N 6.11; Found (%): C 76.02 H 7.52 N 6.09.

EXAMPLE 7

N-(4-Ethoxycarbonylmethylthiazol-2-yl)-$\Delta^8$-dihydroabietamide

M.p. 106°–108° C.

Elem. Anal.: $C_{27}H_{40}N_2O_3S$ (Mol.Wt472.68); Calcd. (%): C 68.61 H 8.53 N 5.93; Found (%): C 68.50 H 9.10 N 6.05.

EXAMPLE 8

N-(4-Carboxymethylthiazol-2-yl)-$\Delta^8$-dihydroabietamide

M.p. 217°–219° C.

Elem. Anal.: $C_{25}H_{36}N_2O_3S$ (Mol.Wt444.63); Calcd. (%): C 67.53 H 8.16 N 6.30; Found (%): C 67.08 H 8.35 N 6.14.

The following pharmacological tests show the effectiveness of the compounds of the present invention.

EFFECT IN CHOLESTEROL LOADED RATS (HCD TEST)

Test method: Male Wister strain rats of 4 weeks age (six rats per group) were used. They were fed with a high-cholesterol food containing 0.03% of the compound to be tested. After 3 days' feeding, they were fasted overnight, blood was collected therefrom, and the total cholesterol level (TC) in serum was measured. A group fed with a high cholesterol food containing no test compound and groups fed with normal synthetic food were called control group and normal groups, respectively. The serum TC increase-inhibiting rate (%) of the test compound was calculated by the following expression:

Inhibitory Rate of TC Increase (%) =

$$100 \times \frac{\text{(Control Group)} - \text{(Test Group)}}{\text{(Control Group)} - \text{(Normal Group)}}$$

The results are set forth in Table 1.

EFFECT IN TRITON-INDUCED HYPERLIPEMIC MICE (TRITON TEST)

Test method: Male ICR-strain mice of 9 weeks age (6 to 9 mice per group) were used. A solution of Triton WR-1339 in physiological saline solution was injected from tail vein at the dose of 500 mg/kg whereupon hyperlipemia was induced. Physiological saline solution was injected to normal group intravenously. Immediately thereafter, 300 mg/kg of the test compound suspended in 0.5% methylcellulose (MC) was given orally. The group given with 0.5% MC solution was called a control group. After fasting for 24 hours, head was cut, blood was taken, and the TC value of the resulting serum was measured. The inhibiting rate (%) against serum TC increase of the test compound was calculated by the following expression:

Inhibitory Rate of TC Increase (%) =

$$100 \times \frac{\text{(Control Group)} - \text{(Test Group)}}{\text{(Control Group)} - \text{(Normal Group)}}$$

The results are set forth in Table 1.

TABLE 1

| Compound Tested | Inhibitory Rate for Cholesterol Increase | |
|---|---|---|
| | (Triton Test) | (HCD Test) |
| Compound of Example 1 | 32** | 115** |
| Compound of Example 3 | 75** | 47** |
| Compound of Example 4 | 68** | 102** |

TABLE 1-continued

| Compound Tested | Inhibitory Rate for Cholesterol Increase | |
|---|---|---|
| | (Triton Test) | (HCD Test) |
| N—(2,6-Dimethylphenyl)-Δ⁸-dihydroabietamide | −8 | 100** |

**Stochastically, significant difference was observed with a 1% level.

It is clear from Table 1 above that the compounds of the present invention exhibit effectivess in the HCD test wherein cholesterol was loaded and in the Triton test wherein cholesterol biosynthesis was accelerated.

ACUTE TOXICITY

Test method: Male mice of STD-ddY strain (6 weeks age) were fasted for 24 hours and then subjected to the test.

A 0.5% methylcellulose suspension of the test compound was given orally, then subjected to usual feeding, and general symptoms and appearance of the dead cases were observed for one week. The result was that all of the present invention compounds tested exhibited low toxicity and administration at a dosage as high as 2 g/kg did not cause any deaths.

It is clear from the above data that the compounds of the present invention exhibit little if any toxicity while exhibiting good inhibitory action against extrinsic cholesterol absorption. In addition, the compounds of the present invention exhibit inhibitory action against cholesterol biosynthesis and catabolism and excretion acceleration. It is clear, therefore, that the compounds of the present invention are useful in the prevention and treatment of hyperlipemia in humans and animals.

What is claimed is:

1. A compound of the formula I

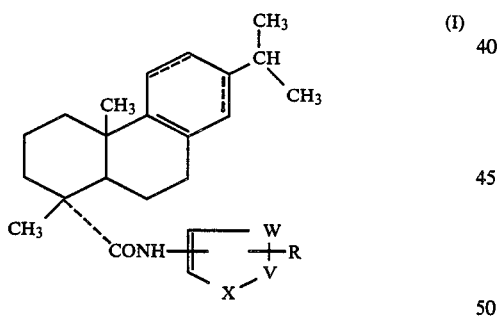

wherein X is NZ wherein Z is hydrogen,, lower alkyl, or phenyl unsubstituted or substituted by halo or lower alkyl; or X is sulphur; when X is NZ, V is nitrogen, W is ⊓, and R is hydrogen or lower alkyl; when X is sulphur, V is ⊔, W is nitrogen, and R is hydrogen, lower alkyl, phenyl or —CH₂COOR' wherein R' is hydrogen or lower alkyl and $\rule[0.5ex]{1em}{0.1ex}$ is a single or a double bond.

2. A compound according to claim 1 wherein X is NZ wherein Z is hydrogen, straight or branch chain alkyl of 1–4 carbon atoms, or phenyl unsubstituted or substituted by halo or alkyl of 1–4 carbon atoms and R is hydrogen or straight or branched chain alkyl of 1–4 carbon atoms.

3. A compound according to claim 1 wherein X is sulphur and R is hydrogen, straight or branch chain alkyl of 1–4 carbon atoms, phenyl or —CH₂COOR' wherein R' is hydrogen or straight or branch chain alkyl of 1–4 carbon atoms.

4. The compound according to claim 1 which is N-(1-phenylpyrazol-5-yl)-Δ⁸-dihydroabietamide.

5. The compound according to claim 1 which is N-(1-Phenylpyrazol-5-yl)dehydroabietamide.

6. The compound according to claim 1 which is N-(1-Methylpyrazol-5-yl)-Δ⁸-dihydroabietamide.

7. The compound according to claim 1 which is N-[1-(2-Chloro)phenylpyrazol-5-yl]-Δ⁸-dihydroabietamide.

8. The compound according to claim 1 which is N-(1-p-Tolylpyrazol-5-yl)-Δ⁸-dihydroabietamide.

9. The compound according to claim 1 which is N-(1-p-Tolylpyrazol-5-yl)dehydroabietamide.

10. The compound according to claim 1 which is N-(1-p-Tolylpyrazol-3-methylpyrazol-5-yl)-dehydroabietamide.

11. The compound according to claim 1 which is 2-Dehydroabietolyamino-4-methylthiazole.

12. The compound according to claim 1 which is N-(Thiazol-2-yl)-Δ⁸-dihydroabietamide.

13. The compound according to claim 1 which is N-(4-Methylthiazol-2-yl)-Δ⁸-dihydroabietamide.

14. The compound according to claim 1 which is N-(Thiazol-2-yl)-dehydroabietamide.

15. The compound according to claim 1 which is N-(4-Phenylthiazol-2-yl)dehydroabietamide.

16. The compound according to claim 1 which is N-(4-Ethoxycarbonylmethylthiazol-2-yl)-Δ⁸-dihydroabietamide.

17. The compound according to claim 1 which is N-(4-Carboxymethylthiazol-2-yl)-Δ⁸-dihydroabietamide.

18. A pharmaceutical composition useful for treating hyperlipemia in humans and animals which comprises a therapeutically effective amount of a compound of the formula I

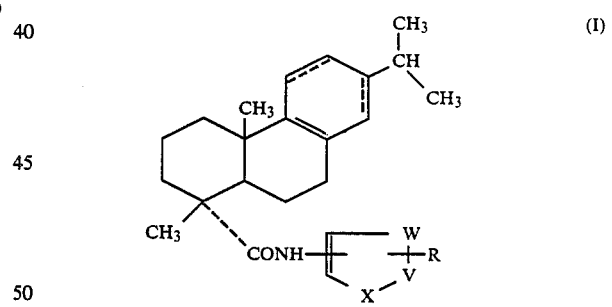

wherein X is NZ wherein Z is hydrogen, lower alkyl, or phenyl unsubstituted or substituted by halo or lower alkyl; or X is sulphur; when X is NZ, V is nitrogen, W is ⊓, and R is hydrogen or lower alkyl; when X is sulphur, V is ⊔, W is nitrogen, and R is hydrogen, lower alkyl, phenyl or —CH₂COOR' wherein R' is hydrogen or lower alkyl and $\rule[0.5ex]{1em}{0.1ex}$ is a single or a double bond, in combination with a pharmaceutically acceptable carrier.

19. A composition according to claim 18 wherein X is NZ wherein Z is hydrogen, straight or branch chain alkyl of 1–4 carbon atoms, or phenyl unsubstituted or substituted by halo or alkyl of 1–4 carbon atoms and R is hydrogen or straight or branched chain alkyl of 1–4 carbon atoms.

20. A composition according to claim 18 wherein X is sulphur and R is hydrogen, straight or branch chain alkyl of 1–4 carbon atoms, phenyl or —CH₂COOR' wherein R' is hydrogen or straight or branch chain alkyl of 1–4 carbon atoms.

21. A composition according to claim 18 wherein the compound is N-(1-phenylpyrazol-5-yl)-Δ⁸-dihydroabietamide.

22. A composition according to claim 18 wherein the compound is N-(1-Phenylpyrazol-5-yl)dehydroabietamide.

23. A composition according to claim 18 wherein the compound is N-(1-Methylpyrazol-5-yl)-Δ⁸-dihydroabietamide.

24. A composition according to claim 18 wherein the compound is N-[1-(2-Chloro)phenylpyrazol-5-yl]-Δ⁸-dihydroabietamide.

25. A composition according to claim 18 wherein the compound is N-(1-p-Tolylpyrazol-5-yl)-Δ⁸-dihydroabietamide.

26. A composition according to claim 18 wherein the compound is N-(1-p-Tolylpyrazol-5-yl)dehydroabietamide.

27. A composition according to claim 18 wherein the compound is N-(1-p-Tolylpyrazol-3-methylpyrazol-5-yl)-dehydroabietamide.

28. A composition according to claim 18 wherein the compound is 2-Dehydroabietolyamino-4-methylthiazole.

29. A composition according to claim 18 wherein the compound is N-(Thiazol-2-yl)-Δ⁸-dihydroabietamide.

30. A composition according to claim 18 wherein the compound is N-(4-Methylthiazol-2-yl)-Δ⁸-dihydroabietamide.

31. A composition according to claim 18 wherein the compound is N-(Thiazol-2-yl)-dehydroabietamide.

32. A composition according to claim 18 wherein the compound is N-(4-Phenylthiazol-2-yl)dehydroabietamide.

33. A composition according to claim 18 wherein the compound is N-(4-Ethoxycarbonylmethylthiazol-2-yl)-Δ⁸-dihydroabietamide.

34. A composition according to claim 18 wherein the compound is N-(4-Carboxymethylthiazol-2-yl)-Δ⁸-dihydroabietamide.

35. A method of treating hyperlipemia in humans and animals which comprises administering to a human or animal in need thereof a therapeutically effective amount of a compound of the formula I

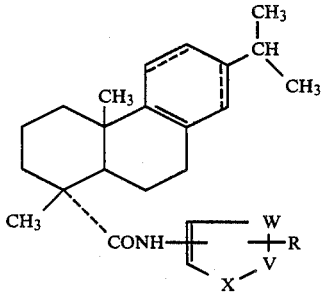

wherein X is NZ wherein Z is hydrogen, lower alkyl or phenyl unsubstituted or substituted by halo or lower alkyl; or X is sulphur; when X is NZ, V is nitrogen, W is ⏋, and R is hydrogen or lower alkyl; when X is sulphur, V is ⎮⎮, W is nitrogen, and R is hydrogen, lower alkyl, phenyl or —CH₂COOR' wherein R' is hydrogen or lower alkyl and === is a single or a double bond, in combination with a pharamaceutically acceptable carrier.

36. A method according to claim 35 wherein X is NZ wherein Z is hydrogen, straight or branch chain alkyl of 1–4 carbon atoms, or phenyl unsubstituted or substituted by halo or alkyl of 1–4 carbon atoms and R is hydrogen or straight or branched chain alkyl of 1–4 carbon atoms.

37. A method according to claim 35 wherein X is sulphur and R is hydrogen, straight or branch chain alkyl of 1–4 carbon atoms, phenyl or —CH₂COOR' wherein R' is hydrogen or straight or branch chain alkyl of 1–4 carbon atoms.

38. A method according to claim 35 wherein the compound is N-(1-phenylpyrazol-5-yl)-Δ⁸-dihydroabietamide.

39. A method according to claim 35 wherein the compound is N-(1-Phenylpyrazol-5-yl)dehydroabietamide.

40. A method according to claim 35 wherein the compound is N-(1-Methylpyrazol-5-yl)-Δ⁸-dihydroabietamide.

41. A method according to claim 35 wherein the compound is N-[1-(2-Chloro)phenylpyrazol-5-yl]-Δ⁸-dihydroabietamide.

42. A method according to claim 35 wherein the compound is N-(1-p-Tolylpyrazol-5-yl)-Δ⁸-dihydroabietamide.

43. A method according to claim 35 wherein the compound is N-(1-p-Tolylpyrazol-5-yl)dehydroabietamide.

44. A method according to claim 35 wherein the compound is N-(1-p-Tolylpyrazol-3-methylpyrazol-5-yl)-dehydroabietamide.

45. A method according to claim 35 wherein the compound is 2-Dehydroabietolyamino-4-methylthiazole.

46. A method according to claim 35 wherein the compound is N-(Thiazol-2-yl)-Δ⁸-dihydroabietamide.

47. A method according to claim 35 wherein the compound is N-(4-Methylthiazol-2-yl)-Δ⁸-dihydroabietamide.

48. A method according to claim 35 wherein the compound is N-(Thiazol-2-yl)-dehydroabietamide.

49. A method according to claim 35 wherein the compound is N-(4-Phenylthiazol-2-yl)dehydroabietamide.

50. A method according to claim 35 wherein the compound is N-(4-Ethoxycarbonylmethylthiazol-2-yl)-Δ⁸-dihydroabietamide.

51. A method according to claim 35 wherein the compound is N-(4-Carboxymethylthiazol-2-yl)-Δ⁸-dihydroabietamide.

* * * * *